United States Patent [19]
Greenfeld et al.

[11] Patent Number: 4,906,238
[45] Date of Patent: Mar. 6, 1990

[54] EXTERIOR ANTIMIGRATION REFINEMENTS FOR SELF-CLEANING INDWELLING THERAPEUTIC ARTICLES

[75] Inventors: Albert R. Greenfeld, 1250 La Venta Dr., Suite 204, Westlake Village, Calif. 91361; Jonathan I. Greenfeld, Westlake Village, Calif.

[73] Assignee: Albert R. Greenfeld, Westlake Village, Calif. ; a part interest

[21] Appl. No.: 96,068

[22] Filed: Sep. 14, 1987

Related U.S. Application Data

[63] Continuation-in-part of Ser. No. 787,728, Oct. 15, 1985, Pat. No. 4,698,058.

[51] Int. Cl.[4] .................................... A61M 25/00
[52] U.S. Cl. ..................... 604/266; 604/22; 604/35; 604/43; 604/265; 604/276
[58] Field of Search ............ 604/22, 35, 43, 264, 604/265, 266, 267, 275, 276; 128/24 A, 303.15, 328

[56] References Cited

U.S. PATENT DOCUMENTS

| | | | |
|---|---|---|---|
| 547,847 | 10/1895 | Thorneton et al. | 604/245 X |
| 2,774,193 | 12/1956 | Thatcher et al. | 128/24 A |
| 3,136,316 | 6/1964 | Beall | 604/43 |
| 3,941,122 | 3/1976 | Jones | 128/24 A |
| 4,176,454 | 12/1979 | Hatter et al. | 128/24 A X |
| 4,698,058 | 10/1987 | Greenfeld et al. | 128/24 A |
| 4,717,379 | 1/1988 | Ekholmer | 604/43 |

FOREIGN PATENT DOCUMENTS

2528273 10/1976 Fed. Rep. of Germany ...... 604/265

Primary Examiner—Carl D. Price
Attorney, Agent, or Firm—Peter I. Lippman

[57] ABSTRACT

External grooving on a catheter traps microorganisms nurtured by mucus in a patient's body. The grooving also traps contaminating debris, originating outside the body, that migrates into the body along the catheter exterior. Energy, which may be a propagating vibration or electrical energy or a radioactive material, is carried to the groove (or grooves), from a source outside the body. This function is performed by a fiber embedded or held in the catheter, or by a liquid column (e.g., in an annular lumen) in the catheter, or in other ways. The energy disables microorganisms and disintegrates debris trapped at the groove. The groove depth, interface geometry, and in the case of vibrational energy the vibration frequency too, are selected to minimize projection of energy into the patient's tissues. Suction may be applied as through an auxiliary lumen (or, in some drain catheters, intermittently through the primary drain lumen itself), to remove resulting detritus at the grooving. Circumferential grooves may be used to impede migration longitudinally, longitudinal grooves to deter formation of continuous circumferential sheets of contaminants, or spiral grooves to lengthen the migration path along the catheter—or combinations of these forms.

11 Claims, 3 Drawing Sheets

EXTERIOR ANTIMIGRATION REFINEMENTS FOR SELF-CLEANING INDWELLING THERAPEUTIC ARTICLES

BACKGROUND

1. Related Application

This is a continuation-in-part of U.S. patent application No. 787,728, which was filed on Oct. 15, 1985, and issued on Oct. 6, 1987, as U.S. Pat. No. 4,698,058.

2. Field Of The Invention

This invention relates generally to indwelling catheters and like articles—e.g., other tubes, and generally other therapeutic articles that remain in a living body for protracted periods.

The invention relates more particularly to systems for keeping the exterior surfaces (as well as any proximal orifices) of such therapeutic articles free of undesirable microorganisms and contaminating debris. Such catheters, tubes and other articles of therapy are used in medical procedures for both humans and animals.

(An "indwelling" catheter or other article is one that is emplaced and left in place for protracted periods, such as fifteen minutes or longer. It has been known to leave catheters in place for more than five years. In this document the word "proximal" is used to define locations with respect to the center of the patient's body, not with respect to the instrumentation at the other end of the catheter. The word "medical" is used to encompass surgical as well as medicinal therapies. The word "bacteria" here encompasses bacteria, viruses, fungi, and other bioactive materials.)

The invention is applicable, for example, to such catheters as the Foley urinary-tract catheter or other urinary catheters, as well as tracheal, cardiac, or central or other venous catheters.

The invention is also suitable for use with tubes that irrigate or drain body cavities such as (without exclusion) the pleural, peritoneal, subarachnoid, intrathecal subdural and intracraneal cavities—or that are used for special procedures such as evacuation of hematoma. Furthermore, as already suggested, our invention is not limited to use with articles having conductive lumens; rather, it can be employed as well with solid rods—either flexible or stiff—that find therapeutic use in medicine.

For illustrative purposes, we shall first discuss at some length the need for our invention in one familiar area. That is the field of catheters which are placed in the urinary tract.

3. Prior Art

A full discussion of prior art with which we are acquainted appears in the patent mentioned above, and in the public record of references adduced and discussed in prosecution of that patent in the United States Patent and Trademark Office.

The invention which is the subject of that patent is addressed primarily to the problems that arise from accumulation of clogging deposits and contaminating bacteria on an indwelling catheter or like article at proximal orifices, and within the interior of such an article. Such deposits and bacteria interfere mechanically and directly with the therapeutic function of a catheter or other tube, and may interfere with the therapeutic functions of various other indwelling articles.

The present document is directed primarily to related problems of formation, multiplication and migration of microorganisms and contaminants on an indwelling article along its outside surface. The interference of such organisms and debris with the function of an indwelling article is neither as mechanical nor as direct, but is equally as severe.

Infections arising from propagation of microorganisms and contaminating debris along the outside surfaces of such articles cause immeasurable grief and enormous costs. These adverse effects are particularly tragic in that they are nosocomial—that is to say, caused during and apparently as a result of hospitalization.

The incidence and cost of nosocomial urinary-tract infections in general hospitals, arising from the use of indwelling catheters, has been reported recently by Rutledge and McDonald in "Cost of Treating Nosocomial Urinary Tract Infections," *Urology* 26 (1 supplemental):24–6, 1985. An earlier discussion was provided by Platt et al., in "Mortality Associated with Nosocomial Urinary Tract Infections," *New England Journal of Medicine* 307:637–642, 1982.

These surveys put the extra hospital time, in a typical instance of nosocomial urinary-tract infection, at five to six days per hospital stay—for an annual nationwide extra cost of 1.8 billion dollars. Nosocomial urinary-tract infections are estimated to arise in 3.6 percent of all hospital admissions. Evans, *Journal of the American Medical Association* 256 (#8 Aug. 22/29), 1986.

The major cause of nosocomial urinary-tract infections in hospitals is believed to be the indwelling catheter. The mortality rate directly attributed to nosocomial bacteremic urinary-tract infection has been reported as 12.8 percent. Furthermore, extensive analysis of hospital histories implicates virtually the entire gamut of procedures for catheter storage, emplacement and maintenance. Refer to *Cecil's Textbook of Medicine*, 17th edition, II:1487 (Saunders), 1985.

In nursing homes, such notorious hazards of urinary-tract infection have apparently deterred the use of urinary catheters on a broad scale, even though such catheters are well known as a means of alleviating the distress of urinary incontinence. Even with such limited use, seven million nosocomial urinary-tract infections—many due to catheter use—occur per year in patients confined to nursing homes (see *Cecil's Textbook of Medicine*).

As a result, elderly patients in nursing homes are generally denied the benefits of such catheters. It is therefore reasonable to consider nursing-home costs arising out of the complications of urinary incontinence. Such costs are estimated in the range $0.5 billion to $1.5 billion per year.

These values represent three to eight percent of all nursing-care costs (see Ouslander, J. G. and Kane, R. L. in "The cost of urinary tract incontinence in nursing homes," *Med. Care* 22:69–79, 1984). Yet, as already suggested, it is generally held that nursing homes would incur greater cost if they put urinary catheters into general use, employing existing catheter-insertion technique.

Problems with indwelling catheters have also been reported in outpatient situations. Indwelling urinary-tract catheters, varying from paraplegic appliances to obstructive-uropathy bypasses, figure prominently in such situations.

Maintenance of urinary catheters is often necessary for paraplegics, as loss of urinary control commonly accompanies their condition. Heretofore such paraplegics have been maintained on virtually constant antibiotic supply, to avoid urinary infection arising from catheterization; even so, their catheters must be changed on a regular basis.

This technique, however, is unhealthy and undesirable as it carries a danger of both tolerance to existing bacteria and bacterial mutation "around" the available antibiotics. Protracted use of each catheter, with little or no antibiotics, could be enjoyed if there were some way to insert and maintain such catheters free of contamination and infection.

Infection costs in this context include medication, increased morbidity, and mortality of other diseases. In this regard please see Platt et al., supra; Edward, "The Epidemiology of 2056 Remote Site Infections," *Annals of Surgery* 6:184, 1976.

In hospitals, nursing homes, and outpatient applications, as shown in the literature, contamination and infection continue to develop after emplacement of an indwelling catheter—even when emplacement has been carried out unreproachably. There are two main mechanisms for such continuing contamination and infection.

First, contaminating debris migrates up and around a catheter from outside the body. Such debris includes fecal fragments, diseased tissue in trace quantities, and so on. Bacteria and other microorganisms are included in, and follow, these substances.

Such contaminants originate from naturally unsanitary regions on the outside of the patient's body but near the distal opening (such as the urethral meatus) of a catheterized duct or incision (e.g., drain site). For purposes of this document, including the appended claims, the term "duct" is to be understood as encompassing any natural passageway into or through the body, regardless of its usual nomenclature. One large contributor to such contamination from outside the body is contamination from the patient's own hands or from the hands of health-care personnel.

Secondly, it is also well recognized that mucous membranes react to an indwelling catheter by secreting mucus. The protein in this mucus forms a nurturing substrate for propagation of bacteria in the space around the catheter, multiplying greatly the overall bacterial population—and, in short, producing an infection in the patient.

Some of the contaminating mechanisms mentioned in the previously mentioned "parent" United States Patent may also contribute to bacterial seeding of the mucous substrate in the space around the outside of an indwelling catheter. These mechanisms consequently aggravate the contaminated conditions in that space.

Furthermore, all of these undesirable conditions may propagate inward into the body via the catheter: they can literally spill over from the proximal end of a catheterized duct or incision into the adjacent cavity (or tissue). By way of example, such a cavity or tissue may be the urinary bladder, or a surgical site.

Contamination of naturally occurring substances within a cavity (e.g., urine in the bladder) and contamination of the cavity wall then ensues. Such an unhealthful sequence may continue with decreasing natural flow or circulation of such substances, in turn promoting further infection as previously noted.

The foregoing summary shows that prior medical art has failed to deal adequately with the problem of infectious media propagating in the spaces or tissue around an indwelling catheter or other therapeutic article. It would be extremely desirable, in terms of quantitative costs as well as human pain and loss, to correct this failing.

This discussion of hospital, nursing-home and outpatient situations makes clear that the need is great for some way to insert and maintain urinary-tract catheters, free from the many sources of contamination discussed above. If indwelling urinary-tract catheters could be inserted and maintained free of contamination and infection for long periods after insertion—the favorable results would include great reductions in infection and human suffering, and save at least hundreds of millions of dollars in time and costs every year.

These data suggest a further conclusion. No problem having such widespread and various causes can be eliminated by any single change in mere medical protocol.

The need is not limited to urinary catheters. A like need exists whenever sterile catheters, tubes, or other elongate articles of therapy are inserted under sterile conditions into a living body. Examples include (among others) pacemakers and central lines (catheters or tubes placed into large veins), as well as Swan-Ganz catheters.

Often these must be inserted under emergency conditions in emergency rooms and intensive- and cardiac-care units. In these situations sterility is too easily compromised.

SUMMARY OF THE DISCLOSURE

Our invention is a self-cleaning indwelling therapeutic-article system. It is for protracted use in an extended condition within a patient's body.

In other words, the invention provides a self-cleaning therapeutic article that is extended within some portion of a human or animal patient's body, and is used in that condition for protracted periods of time.

The phrase "extended condition within" or "extended within" is to be understood as encompassing extension of the therapeutic article through a surface of the patient's body, so that the article is partially inside and partially outside the body—as well as extension of the article between two locations that are both within the body.

Thus the invention may for example include a self-cleaning catheter for use in protracted transfer of substance between a patient's body and a point outside the patient's body.

The invention includes a therapeutic article for such protracted use. The article has an external surface that is subject to the presence and propagation of undesirable microorganisms during use—for example, in the case of a catheter, during such protracted substance transfer. A shallow groove is defined or formed in the external surface of the article.

The invention also includes a source of energy. In addition, the invention must include some means for conveying the energy from the source to the groove—to disable undesirable microorganisms at the groove. For purposes of broad generality in expressing our invention, we shall call these means the "energy conveying" means.

Because the energy disables such microorganisms, it may accordingly be termed "disabling energy." (We do not mean to suggest, of course, that the energy necessarily disables every individual microorganism.) By disabling the microorganisms, the energy deters their propagation, and significantly enhances the sanitary and healthful protracted use of the therapeutic-article.

The energy may be in any one or more of several forms, particularly (but without limitation) including propagating vibrations of various kinds. We now prefer to use mechanical vibration such as ultrasonic acoustic vibration; however, our invention contemplates substituting other forms of vibration including electromagnetic radiation (ultraviolet, visible and infrared radiation, or in principle even x-rays or radio-frequency waves).

Still other forms of energy that may be employed include (still without limitation) electrical voltage or current, and radioactivity. Our invention encompasses the use of any form of energy that can be safely conveyed along the therapeutic article and applied at its external groove to disable the undesirable microorganisms.

The foregoing description may provide a definition of our invention in its broadest form. We prefer, however, to incorporate certain additional characteristics or features to optimize enjoyment of the several benefits of the invention.

In particular, the groove may include at least one generally circumferential depression passing substantially around the therapeutic-article periphery. The groove may include a generally spiral depression passing substantially around and along the article at an angle to the article length. The groove preferably includes both circumferential and spiral depressions. These preferably intersect.

In addition to living bacteria, the exterior surface of an indwelling therapeutic article is also subject to accumulation and passive migration of contaminating debris—including mucus and externally introduced contaminants, as discussed earlier. The vibration introduced as described above tends to disintegrate such debris, regardless of source, and tends to disintegrate disabled microorganisms as well.

The system of our invention adantageously also includes a suction apparatus or subsystem for drawing off such contaminating debris or microorganisms, or both, after action by the disabling and disintegrating vibration. The suction system can be operated through a secondary lumen in the therapeutic article, or in some cases (as will be explained) through the primary lumen.

Depending upon the type of disabling energy employed, the conveying means may include a plastic, metal, quartz or other fiber, embedded or carried within the therapeutic article. The fiber may have a termination at the groove, or may pass along the groove—conveying the energy to the groove at the base or sides of the groove. Alternatively a liquid column or other means may be employed to convey the energy to the groove.

Our invention contemplates particularly adapting the depth and configuration of the groove for safety of the patient from any destructive effects of the energy. In particular it is a part of our invention to so adapt the groove, in relation to the configuration of the conveying means, to deter projection of the energy outward from the groove into tissues of the patient's body in significant (i.e., harmful) quantity.

When the energy employed has some vibratory form, then this adaptation of the groove preferably also takes into account the relation of the groove shapes and dimensions to employed frequencies of the vibration. Resonance and damping phenomena that come into play in this regard are well understood among skilled designers of, for example, ultrasonic mechanical-vibration equipment.

Our invention can eliminate or at least alleviate the previously presented problems of infection and secondary effects that arise from the use of indwelling therapeutic articles. It therefore may greatly enhance the benefit of medical treatments requiring such articles, and may accordingly confer broad benefits on patients afflicted by any of a very large variety of conditions.

All the foregoing principles and advantages of the present invention will be more fully appreciated upon consideration of the following detailed description, with reference to the appended drawings, of which:

DETAILED DESCRIPTION OF THE PREFERRED EMBODIMENTS

Figure 1:
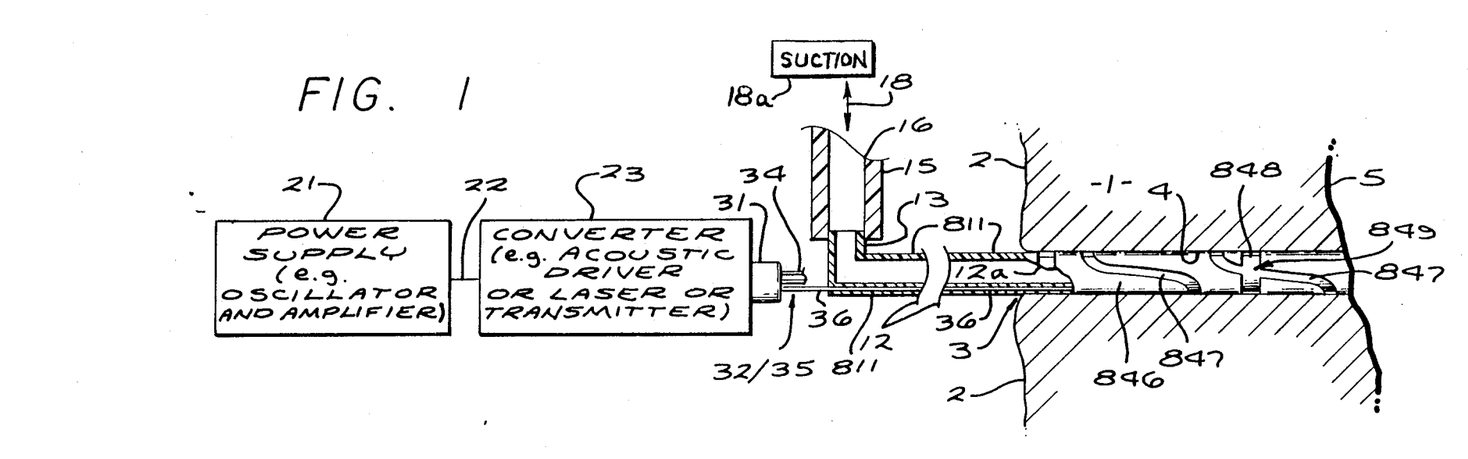
FIG. 1 is a generally schematic representation of a preferred embodiment of our invention in use. In this embodiment the therapeutic article is a catheter or other tube.

As shown in FIG. 1, a preferred embodiment of our self-cleaning indwelling therapeutic-article system includes a suitably powered device 21-23 for developing a flow of energy in appropriate form for projecting along the therapeutic article. In the case of electromagnetic vibration, for example, the device 21-23 may include a power supply 21, transmitting electrical power as at 22 to a high-power pulse laser, microwave transmitter or x-ray generator 23.

If a laser is used at 23, its output may be coupled to one or more optical fibers 32/35 for transmission to the locations along the article where energy is to be applied for disabling of bacteria. If radio-frequency or x-ray radiation is used, analogous provision must be made for conveying and constraining the energy along the therapeutic article without injurious leakage to the patient's body tissues.

As will now be clear, the many forms of energy that might be used to disable bacteria are not all equally amenable to such transmission. In fact some individuals who are skilled in the art may judge implementation of the two forms just mentioned to be so difficult or so costly as to be noneconomic for many purposes. Nevertheless, to the extent that they do have practical uses for particular situations, such forms are encompassed within our invention.

Alternatively, in the case of energy in the form of electricity, the device 21-23 may simply be a power supply for transmitting electrical voltage along wire pairs into the therapeutic article. In the case of mechanical vibration, by comparison, the device 21-23 includes an oscillator and amplifier 21, whose output 22 energizes an electromechanical driver 23. The driver may take any of a variety of forms, particularly including but not limited to piezoelectric, electromagnetic and dynamic-capacitive.

The output of such a driver 23 is mechanical vibration in a manifold bar, rod or the like 31. For some embodiments of our invention, this vibration is advantageously coupled to a plurality of individual vibration-conveying elements 32/35.

These conveying elements 32/35 may include a plurality of elements 32 for carrying cleansing (i.e., disabling and disintegrating) vibration to proximal drain or medication-supply orifices. Various such configurations are detailed fully in the above-mentioned patent.

It is to be understood throughout the present description that the vibration source used for vibrationally cleansing the exterior of a catheter, as herein described, may thus be advantageously shared with conveying elements 32 for vibrationally cleansing the proximal orifices. If preferred, however, separate vibration sources may be used.

In some applications, moreover, it may be desired to use a vibration source for cleansing the exterior of a catheter while vibrational cleansing of proximal orifices is omitted. All such possibilities are to be understood as incorporated by reference into the following discussion and illustrations.

For relative simplicity of the following descriptions and appended drawings, provision for application of vibration to proximal orifices has been uniformly omitted. Thus in FIG. 1 the conveying elements 32 for the orifices are shown terminated as at 34.

Of the numerous remaining conveying elements 35 for vibrational cleansing of the outside of the catheter, again for simplicity only a single representative conveying element 36 is shown in FIG. 1 as continuing into the catheter 811. The catheter 811 has an attachment nipple 13, which may be angled as shown to permit lateral attachment of liquid-carrying tubing 15 while vibration is coupled to the catheter with less-abrupt change of direction.

Liquid is transmitted in or out of the catheter 811 through the tubing 15 as suggested by the double-headed arrow 18. An optical suction device 18a, inter alia, may be connected to the tubing 15, for use as discussed later. For simplicity of the drawing, the tubing 15 is drawn as terminated at 16.

Also for convenience in illustration, a length of the tubing 811 has been omitted between the points 12 in FIG. 1. Thus the equipment 21-35 and 13-18 may be at some convenient distance from the body 1 of a patient—and particularly from the exterior surface 2 of the body, and from the distal aperture 3 (such as a urethral meatus) of the duct or incision 4 to be catheterized.

The catheter 811 may continue at some considerable distance into the patient's body 1. In addition, the phenomena that are of particular interest for purposes of this document occur along the shaft of the catheter 811—most generally without regard to distance from the distal aperture 3, although to some extent the more important regions are more distal.

For these reasons the proximal portions of the catheter 811, the patient's body 1, and the duct or incision 4 have all been drawn in FIG. 1 interrupted as at 5.

In FIG. 1 the portions of the catheter 811 that are outside the patient's body 1, as well as the nipple 13 and tubing 15, are shown in section. The catheter outer surface 846, however, is illustrated in elevation, along most of the portion that is shown inside the patient's body 1. The transition between the sectional portions and the exterior-elevational portions is designated as 12a.

The region of particular interest in FIG. 1 is the very irregular but generally annular volume between the exterior surface 846 of the catheter and the interior surface 4 of the duct (as defined above) or incision. It is in this region that mucus is secreted (particularly in the case of mucous-membrane ducts). It is in this region too that contaminating debris tends to migrate inwardly from the unsterile ambient environment.

Figure 2:
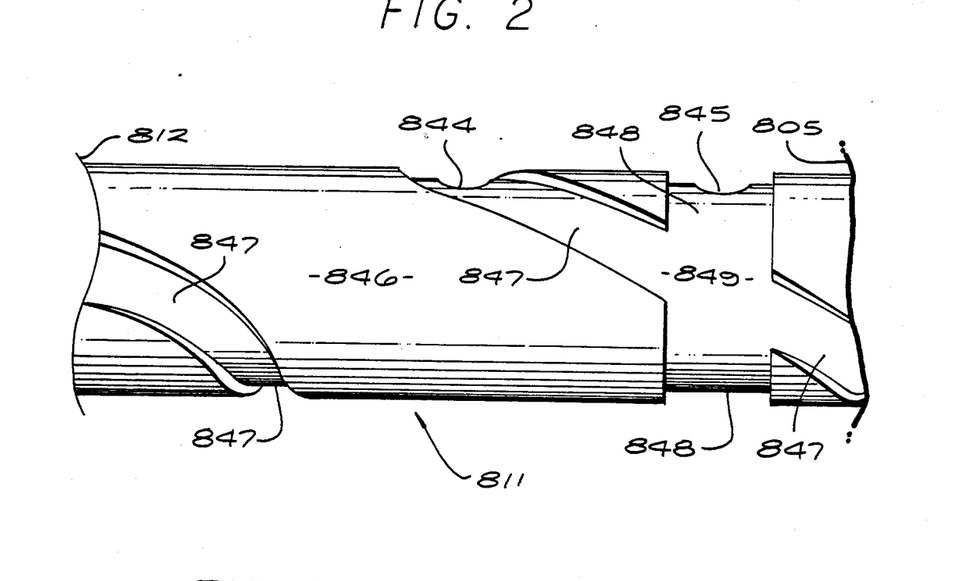
FIG. 2 is a perspective drawing, greatly enlarged but not to scale with respect to the groove depth, of a segment of the catheter portion of the FIG. 1 system. The segment illustrated is one which, in use, is within a patient's body.

Formed in the outside surface 846 of the catheter 811, as shown in FIGS. 1 and 2, is a shallow groove or groove network 847-849. This groove 847-849 includes at least one circumferential depression 848 and at least one spiral depression 847. For some applications these depressions may come together in an intersection or intersections 849.

Groove depths and widths will vary with the type of energy source used and when applicable its frequency, and also with different patient-tissue types, the type of bacteria or debris of greatest concern, and other factors. For mechanical vibration, we believe that adequate cleansing can be obtained, without projecting significant energy into surrounding tissues, by employing a groove depth on the order of two millimeters.

This order of magnitude appears in keeping with the results of ultrasound tissue-attenuation measurements reported for a different medical application by Joie P. Jones, in U.S. Pat. No. 3,941,122. In Jones' experiments, a one-degree maximum rise in temperature appeared at a distance of two millimeters from an ultrasound transducer used for dissolving various organic materials.

A sizable plurality of circumferential grooves 848 may be provided. As will be seen, these circumferential grooves 848 trap and interfere positively with colonization and migration of contaminants along the catheter, and should be disposed for optimum overall impact upon the contaminant problem.

Our invention contemplates instrumenting each groove for the disabling energy—electromagnetic or mechanical vibration, electricity, etc. as previously discussed. Furthermore, other costs will be associated with placement of each groove. It is thus desirable to form only enough grooves to achieve the intended benefits.

For example, such grooves may be placed at regular intervals (e.g., one-inch intervals) along the catheter. Alternatively, they may be placed at relatively short intervals in regions (e.g., near the aperture 3) where contaminant propagation is particularly severe, and at relatively long intervals in less-critical regions.

FIG. 2 representatively includes two spiral grooves 847. Such grooves may be maintained in a mutually diametrical relationship, relative to the body of the catheter, or as suggested in the illustration may have a generally arbitrary relationship.

Spiral grooves—also instrumented for vibration—tend to lengthen the migration path for contaminants, and also prevent the formation of a continuous sheath of contaminants entirely encircling the catheter. The spiral grooves also trap and destroy some contaminants.

We have not determined experimentally the relative benefits of spiral and circumferential grooves. For deeper or more abruptly contoured grooves, however, it is possible that spiral patterns may be preferable to circumferential, for minimum patient discomfort.

Longitudinal grooves have some of these beneficial effects of spiral grooves, but as will be apparent do not lengthen the migration path. Though not specifically illustrated, longitudinal grooving is to be taken as shown by implication: a longitudinal groove is in effect a special case of spiral groove, with zero angle of inclination to the catheter axis.

Our invention encompasses provision of suction apertures 844, 845 at intervals along the grooves 847-849. These apertures, and a suction system (see, e.g., FIG. 1) connected to the catheter outside the patient's body, cooperate to remove the products of action of vibration or other disabling and disintegrating energy applied to the grooves 847-849.

Several representative arrangements for applying energy and suction to the grooves 847-849 will now be discussed.

Figure 3:
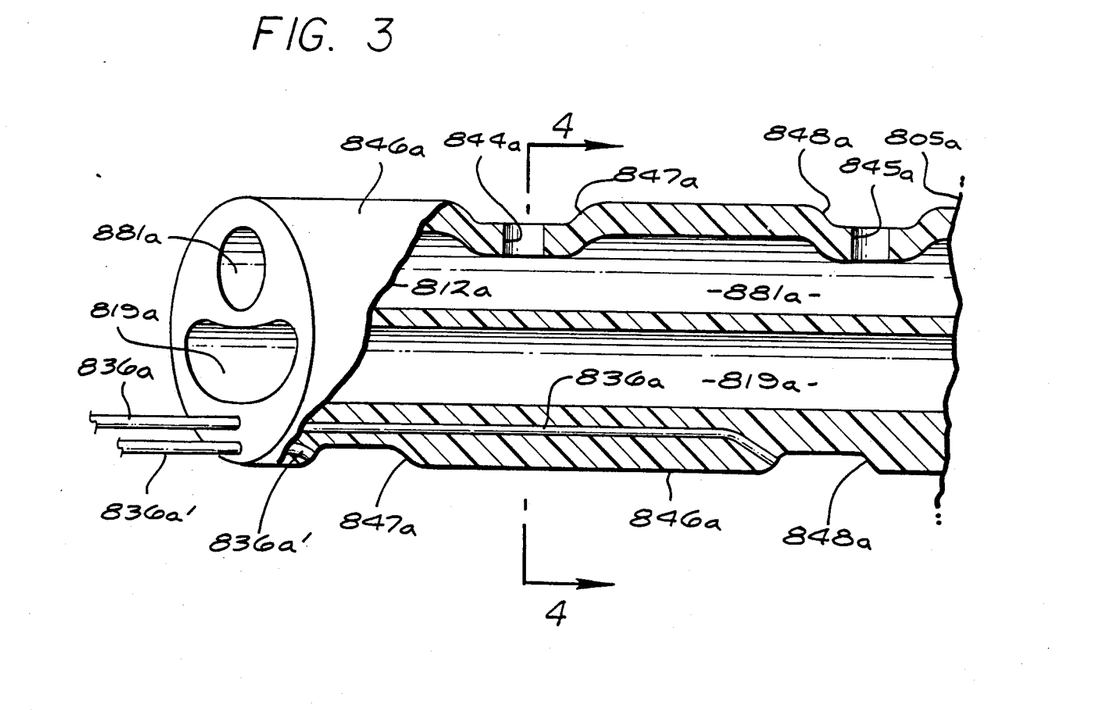
FIG. 3 is a longitudinal section of one form of the preferred embodiment of FIGS. 1 and 2, particularly showing the same segment of the catheter as in FIG. 2. This form of the preferred embodiment employs an embedded fiber as part of the conveying means, and an auxiliary lumen for applying suction.
Figures 4, 6:
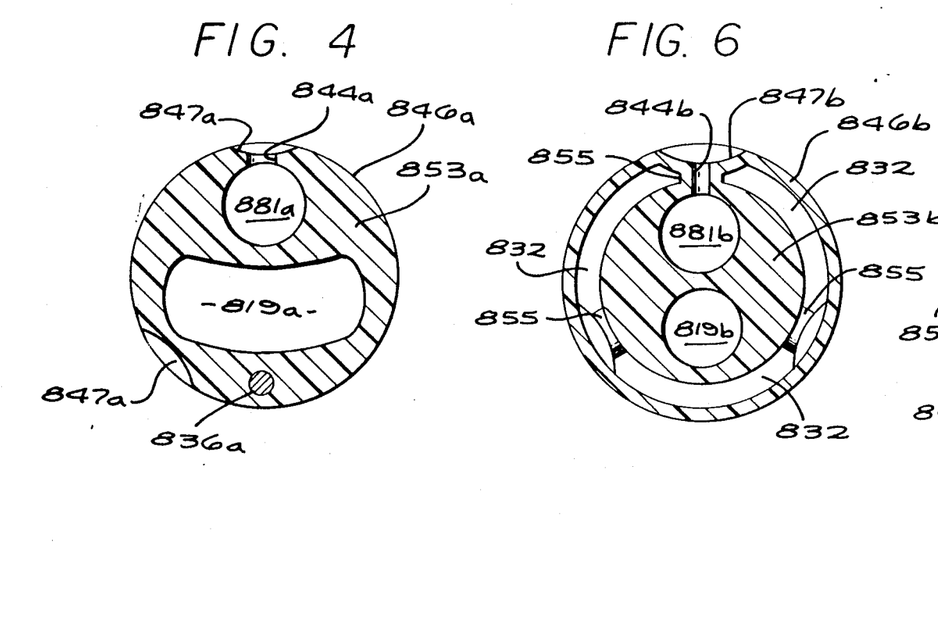
FIG. 4 is a cross section of the FIG. 3 form, taken along the line 4—4 in FIG. 3.
FIG. 6 is a cross section of the FIG. 5 form, taken along the line 6—6 in FIG. 5.

As shown in FIGS. 3 and 4, vibration or other forms of energy may be conveyed from the manifold bar 31 of FIG. 1 to each groove 847a, 848a by a separate fiber 836a, 836a'. Each fiber 836a, 836a' may be embedded within the catheter wall as shown, and terminated at its respective groove 847a, 848a—directed either toward the side wall or toward the bottom wall of the groove. Alternatively for some applications, as mentioned earlier, the fibers may pass adjacent to the groove, without termination there.

Various fiber materials may be used, depending on frequency when applicable, and on form of energy, power level, therapeutic-article size, the kind and size of patient and site, etc. Plastic, metal and quartz are among the candidate materials.

It is believed that the optimum location of the fiber termination or course relative to the groove for each application can be found with moderate trial and error. Such a location may for example be near the "corner" formed by the base and bottom walls.

An important part of implementing our invention is avoiding patient injury due to projection of vibration into the patient's body tissues. The exact geometry chosen for coupling vibration from the fiber to the groove is expected to be of considerable importance for safety. One possible configuration that may be particularly safe, but whose efficacy in disabling bacteria remains to be seen, is a fiber that runs adjacent—and possibly parallel—to the groove, without termination at the groove.

Hence the evaluation of performance for each fiber-groove configuration must include measurements of energy coupling into surrounding tissue. Such measurements should be made in test circumstances reasonably simulating actual operating conditions.

Figure 7:
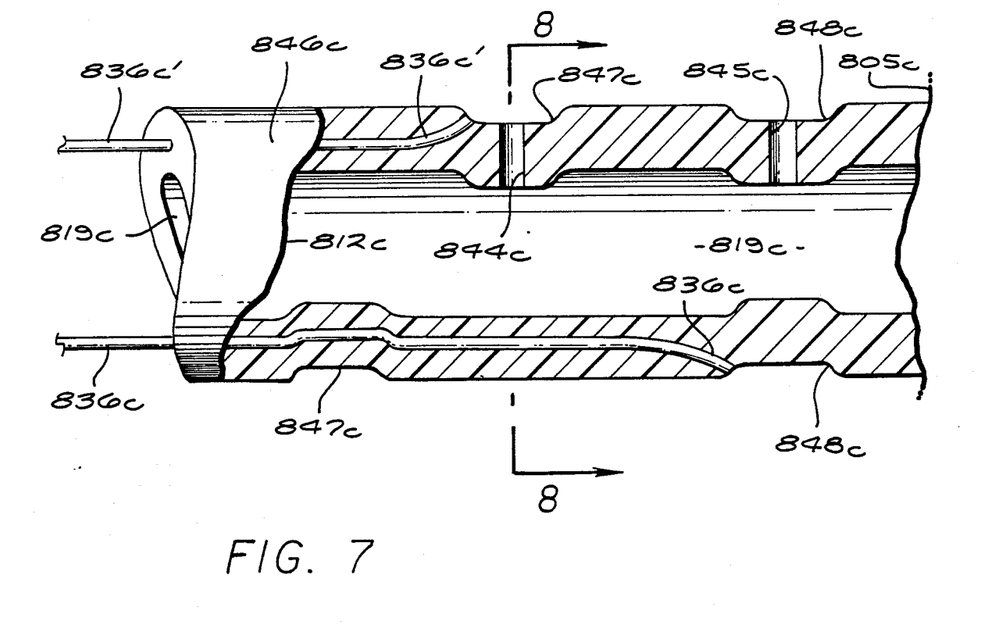
FIG. 7 is a longitudinal section of another form of the preferred embodiment of FIGS. 1 and 2, also showing the same segment of the catheter as in FIG. 2. This form of the preferred embodiment employs the primary lumen for application of suction.
Figure 8:
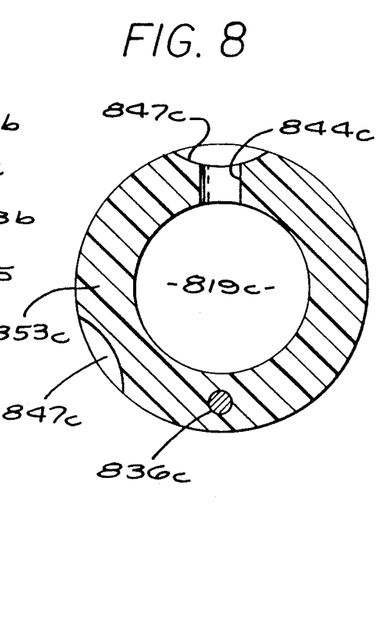
FIG. 8 is a cross section of the FIG. 7 form, taken along the line 8—8 in FIG. 7.

The vibration-conveying provisions of FIGS. 3 and 4 are closely paralleled in FIGS. 7 and 8. In those latter drawings, corresponding or analogous features have been marked with the same reference numerals as used in FIGS. 3 and 4—but with a suffix "c" instead of "a".

In the embodiment of FIGS. 3 and 4, however, a separate suction lumen 881a is provided for drawing off disabled and disintegrated organisms, or disintegrated debris, from the grooves 847-849. In other words, the previously mentioned external suction orifices 844 and 845 of FIG. 2, here represented as 844a and 845a, communicate inside the catheter with a separate suction lumen 881a.

This form of our invention allows uninterrupted continuing operation of the primary lumen 819a for drainage or medicament supply. Such operation may optimize the effectiveness of any self-cleaning mechanisms at the proximal orifices.

On the other hand, as is particularly clear from FIG. 4, this configuration does to some extent limit the range of circumferential positions available for use in forming suction ducts communicating with the grooves. Moreover, a dual-lumen catheter may be somewhat more costly, and for the same external gauge requires greater care (as, for example, application of more disintegrating energy in accordance with our above-mentioned earlier patent) to prevent clogging, than a single-lumen catheter.

All three of these limitations are avoided in the geometry of FIG. 8, which is suitable for use in some drain applications, and in some other applications not requiring sterility within the primary lumen of the catheter. Here suction is applied (as indicated in FIG. 1) to the primary lumen, from time to time, to draw off disabled and disintegrated organisms, or disintegrated debris, from the grooves 847c-849c.

In the embodiment of FIGS. 7 and 8 it may be necessary to strike a careful balance between the size and configuration of the orifices 844c, 845c at the grooves 847c, 848c, and the size and configuration of the proximal orifices (not illustrated) nearer the proximal end of the catheter. This is important to avoid drawing debris into the proximal orifices, in excess of what can pass through those orifices or what can be handled by the disabling- and disintegrating-energy arrangements there.

Figure 5:
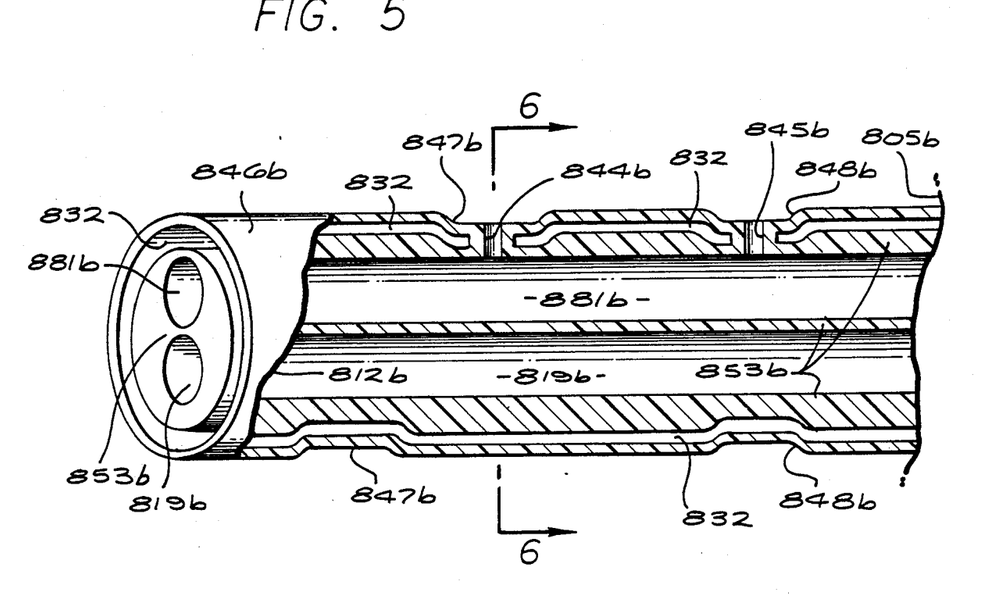
FIG. 5 is a longitudinal section of another form of the preferred embodiment of FIGS. 1 and 2, also showing the same segment of the catheter as in FIG. 2. This form of the preferred embodiment employs a liquid column in an auxiliary lumen as part of the conveying means, and another, separate auxiliary lumen for applying suction.

Another way of conveying energy to the trapping grooves 847b, 848b is illustrated in FIGS. 5 and 6. Here the conveying means includes a separate lumen 832, preferably an annular lumen as shown. Energy is coupled from the manifold 31 (FIG. 1) through a fixture (not illustrated) to a column of liquid within this lumen.

The lumen may advantageously be made relatively narrow, and the exterior wall enclosing it relatively thin, so that the lumen traverses a distinct step at each groove. It is contemplated that the resulting "water hammer" effect, at the interior side of the wall and undersurface of each groove, will couple energy from the liquid column to materials trapped in the groove.

The conveying means shown in FIGS. 5 and 6 may have a particular benefit—use of the same annular or other lumen to supply energy to the trap grooves and the proximal orifices in common. Formation of the suction-bridge ducts 844b, 845b may be difficult or expensive, but may be favorable in comparison with embedding and terminating a large number of plastic, metal or quartz fibers.

The embodiment of FIGS. 5 and 6 may have, as illustrated, a separate suction lumen 881b analogous to the already discussed suction lumen 881a of FIG. 4. If preferred, however, a unitary drainage-and-suction lumen (not illustrated) like that of FIG. 8 may be substituted.

For the various reasons presented at length in the above-mentioned patent, we prefer to use shear-wave vibration at ultrasound or adjacent frequencies; and vibration-conveying means in the form of quartz fibers, for most applications not over one to two millimeters in diameter. Similarly, the timing of patient vibration exposure should be considered carefully and may be monitored in sensitive cases; and feedback and servocontrolled frequency hunting as described in our earlier patent may be included in the system at the trap grooves. Other features of the above-mentioned patent may be included as appropriate, in the system disclosed here.

While for particularity our invention has been illustrated in use with catheters or like tubes, it is to be borne in mind that nonlumenal articles of therapy are also subject to the benefits of the invention.

It will be understood that the foregoing disclosure is intended to be merely exemplary, and not to limit the scope of the invention—which is to be determined by reference to the appended claims.

We claim:

1. A self-cleaning indwelling therapeutic-article system, for protected use in an extended condition within a patient's body, the article passing between tissues of a duct or incision in the patient's body; said system comprising:
   a therapeutic article that has a periphery and a length, and that during indwelling use:
      passes through such duct or incision,
      includes a part of said length that is inside such patient's body,
      includes a portion that is closely encircled by such duct or incision tissues, and
      defines an external surface that is subject to the presence and propagation of undesirable microorganisms, along the portion that is closely encircled by tissues of such duct or incision;
   a shallow groove defined in the external surface of the article to trap and interfere with migration of contaminants, said groove being defined along at least the portion that is closely encircled by tissues of such duct or incision during such use; wherein the groove comprises:
      a generally circumferential depression that passes substantially around the article periphery; and
      a generally spiral depression that passes substantially around and along at least a part of the article length that is inside such patient's body;
   a source of effective disabling energy; and
   means for conveying the energy from the source to the contaminant-trapping groove to effectively disable such undesirable microorganisms at the contaminanttrapping groove and deter such propagation along the portion that is closely encircled by tissues of such duct or incision during use.

2. The system of claim 1, wherein:
the generally spiral depression intersects the circumferential depression.

3. A self-cleaning catheter system, for use in protracted transfer of substance between a patient's body and a point outside such patient's body, by way of passage between tissues of a duct or incision in the patient's body, and comprising:
   a catheter that defines an internal lumen for such protracted transfer of substance, and that:
      during such protracted transfer passes through such duct or incision,
      includes a portion which during such protracted transfer is closely encircled by such duct or incision tissues,
      defines an external surface that is subject to the presence and propagation of undesirable microorganisms, during such protracted transfer, along the portion that is closely encircled by tissues of such duct or incision, and also subject to accumulation and passive migration of contaminating debris along that portion;
   a shallow groove defined in the external surface of the catheter to trap and interfere with migration and propagation of debris and microorganisms, said groove being defined along at least the portion that is closely encircled by tissues of such duct or incision during such protracted transfer and including:
      a generally circumferential depression that passes substantially around the catheter periphery, and
      a generally spiral depression that passes substantially around and along at least a part of the catheter length that is within such patient's body;
   a source, disposed outside such patient's body, of effective disabling and fragmenting energy; and
   means for conveying the energy from the source to the trapping groove to effectively disable such undesirable microorganisms at the trapping groove and deter such propagation along the portion that is closely encircled by tissues of such duct or incision during such protracted transfer, and to fragment such debris at the groove.

4. The system of claim 3, wherein:
the catheter has a long axis; and
the generally spiral depression has at least one segment that runs substantially perpendicular to the long axis of the catheter.

5. The system of claim 4, wherein:
the generally spiral depression intersects the circumferential depression.

6. The system of claim 4, wherein:
the catheter has a long axis; and
the generally spiral depression intersects the circumferential depression and has at least one segment that runs substantially perpendicular to the long axis of the catheter.

7. The system of claim 4, further comprising:
suction means for drawing off such microorganisms, or such debris or fragmented debris, or combinations of all three, from the groove.

8. The catheter system of claim 3, wherein:
the conveying means comprise a fiber embedded or carried within the catheter.

9. The catheter system of claim 3, wherein:
the conveying means comprise a fiber embedded or carried within the catheter and having a termination at the groove.

10. The catheter system of claim 3, wherein:

the conveying means comprise a fiber embedded or carried within the catheter and running adjacent to the groove.

11. The catheter system of claim 3, wherein:

the energy is in the form of a propagating vibration; and the depth and configuration of the groove, in relation to the configuration of the conveying means and in relation to employed frequencies of the vibration, are particularly adapted to deter significant projection of the vibration out from the groove into tissues of the patient's body.

* * * * *